US012591964B2

(12) United States Patent　　　　　(10) Patent No.:　US 12,591,964 B2
Maria Galamba Ferrari Calisto et al.　　(45) Date of Patent:　Mar. 31, 2026

(54) CORRELATING GEOMETRIC SHAPES OF SEGMENTED REGIONS BY AT LEAST TWO DIFFERENT IMAGING TECHNOLOGIES FOR IMPROVED IDENTIFICATION OF BREAST LESIONS

(71) Applicant: INSTITUTO SUPERIOR TÉCNICO, Lisbon (PT)

(72) Inventors: Francisco Maria Galamba Ferrari Calisto, Lisbon (PT); Jacinto Carlos Marques Peixoto Nascimento, Odivelas (PT)

(73) Assignee: INSTITUTO SUPERIOR TECNICO, Lisbon (PT)

( * ) Notice: Subject to any disclaimer, the term of this patent is extended or adjusted under 35 U.S.C. 154(b) by 392 days.

(21) Appl. No.: 18/029,407

(22) PCT Filed: Sep. 27, 2021

(86) PCT No.: PCT/PT2021/050029
§ 371 (c)(1),
(2) Date: Mar. 30, 2023

(87) PCT Pub. No.: WO2022/071818
PCT Pub. Date: Apr. 7, 2022

(65) Prior Publication Data
US 2023/0360202 A1　　Nov. 9, 2023

(30) Foreign Application Priority Data
Sep. 30, 2020　(PT) ........................................ 116801

(51) Int. Cl.
G06T 7/00　　　(2017.01)
G06T 7/11　　　(2017.01)
(Continued)

(52) U.S. Cl.
CPC .............. G06T 7/0012 (2013.01); G06T 7/11 (2017.01); G06T 7/60 (2013.01); G16H 30/40 (2018.01);
(Continued)

(58) Field of Classification Search
CPC . G06T 7/0012; G06T 7/11; G06T 7/60; G06T 2207/10072; G06T 2207/30068;
(Continued)

(56) References Cited

U.S. PATENT DOCUMENTS

2003/0007598 A1 *　1/2003　Wang ..................... A61B 6/463
378/37
2006/0274924 A1　12/2006　West et al.
(Continued)

FOREIGN PATENT DOCUMENTS

EP　　　　2272434 A1　　1/2011
WO　　2019210292 A1　　10/2019

*Primary Examiner* — Christopher Wait
(74) *Attorney, Agent, or Firm* — Rivka Friedman

(57)　　　　　　ABSTRACT

The present invention falls within the field of medical imaging, specifically imaging aimed at identifying breast lesions, specifically, identifying potential breast cancer lesion masses or potential cancer lesion calcifications of the breast. The object of the present invention is a computational method for the improved identification of breast lesions that involves obtaining digital images of a breast section, with at least two digital images obtained by different imaging technologies, their segmentation and consequent correlations, to identify one or more cancer lesions. This allows for improved automation of the identification of breast lesions.

10 Claims, 3 Drawing Sheets

Type text here

(51) Int. Cl.
G06T 7/60 (2017.01)
G16H 30/40 (2018.01)
(52) U.S. Cl.
CPC ............... *G06T 2207/10072* (2013.01); *G06T 2207/30068* (2013.01); *G06T 2207/30096* (2013.01)
(58) Field of Classification Search
CPC . G06T 2207/30096; G06T 2207/10088; G06T 2207/10116; G06T 2207/10132; G06T 2207/20084; G06T 2207/20092; G06T 7/00; G16H 30/40; G16H 30/00
See application file for complete search history.

(56) References Cited

U.S. PATENT DOCUMENTS

| | | | | |
|---|---|---|---|---|
| 2006/0274928 A1* | 12/2006 | Collins | ................. | G16H 30/40 382/132 |
| 2021/0035296 A1* | 2/2021 | Mahrooghy | ........... | G06V 10/25 |

* cited by examiner

CORRELATING GEOMETRIC SHAPES OF SEGMENTED REGIONS BY AT LEAST TWO DIFFERENT IMAGING TECHNOLOGIES FOR IMPROVED IDENTIFICATION OF BREAST LESIONS

FIELD OF THE INVENTION

The present invention falls within the field of medical imaging, specifically imaging aimed at identifying breast lesions, thereby identifying potential breast cancer lesion masses or potential breast cancer lesion microcalcifications.

BACKGROUND OF THE INVENTION

Breast cancer is the most common cancer in women worldwide, with nearly 1.7 million new cases diagnosed in 2012, representing 12% of new cancers and 25% of all 166 types of cancer in women. According to the article "*The efficacy of using computer-aided detection (cad) for detection of breast cancer in mammography screening: a systematic review*", Henriksen, E. et al, Acta Radiologica, 2018.

The diagnosis of medical imaging is a routine effort performed by radiologists to help diagnose or monitor a medical condition. Medical imaging diagnosis allows physicians to identify pathologies by decoding tissue characteristics while examining patients' cases in medical images. It plays a central role across modern medicine, in particular for the prevention and diagnosis of cancer, which is one of the leading causes of mortality worldwide.

Breast cancer screening plays a key role in reducing mortality, with a high convenience rate. Early diagnosis of asymptomatic patients allows for intervention and treatment, reducing mortality rates for cancer patients.

A more widely used form of imaging for breast screening is MammoGraphy (MG). However, there is a high risk of medical error without the use of UltraSound (US), commonly known as ultrasound, or Magnetic Resonance Imaging (MRI) in dense breast situations, which is quite common. It is, therefore, difficult to establish a connection or diagnose problems with just one modality.

The screening workflow can thus involve multiple imaging modalities, including MG, in both CranioCaudal (CC) and MedioLateral Oblique (MLO) views, UltraSound (US) and Magnetic Resonance Imaging (MRI) volumes. Response rates and costs of multiple variations (i.e., each modality) have an inherent risk of a higher rate of medical error to the patient and increased costs associated with unnecessary biopsies.

Deep Learning (DL) algorithms are increasing the quality of automatic medical diagnosis, at the cost of creating datasets to train and test these supervised Machine Learning (ML) methods. In the radiology room, annotating medical images is one of the main activities of radiologists and the quality of the annotation depends on the clinician's experience and the number of cases studied.

The US patent with publication number U.S. Pat. No. 7,308,126 discloses a solution representative of the prior art, including output screens from a Computer Aided Detection (CADe) system that allows providing accurate representations of areas for subsequent examinations. As the CADe output is not used during the initial diagnostic, a label is not performed until a final conclusion is reached, which reduces system performance. In addition, the denoted regions are shown in the context of a specific anatomical detail. This solution assists the clinician, other physicians and patients by locating the exact area for subsequent exams, however, it does not provide an improved way to automate the process of identifying breast lesions.

U.S. patent Publication Number U.S. Pat. No. 8,164,039 discloses a method and apparatus for detecting one or more spiculated masses in an image using a processor. This solution includes the use of medical imaging technologies, namely in the field of breast cancer, and addresses the resources for recording injuries in the MG modality from a remote environment. Despite these advantages, the work does not cover a multimodality strategy, as it focuses only on the mammography modality and, like the previous document, it does not allow for automation of detection, not covering the standardized generation of a dataset with annotations in medical images.

Even considering state-of-the-art solutions, proper classification, location, detection, segmentation and recording of tumors are improved by using different imaging modalities that contribute to diagnostic reliability.

The solution of the present invention includes the efficient extraction of image resources from different imaging technologies, enabling an improved automation for the identification of breast lesions.

SUMMARY OF THE INVENTION

It is thus an object of the present invention a computational method for the improved identification of breast lesions characterized by comprising the steps of:
  a) obtaining a plurality of digital images of a breast section, at least two of these images being obtained by distinct imaging technologies,
  b) registering one or more regions of interest from the digital images of a breast section, to be identified,
  c) segmenting sections, thus obtaining segmented regions,
  d) correlating the segmented sections of the various digital images and,
  e) based on that correlation, identifying one or more breast lesions.

The present solution, thus, allows an efficient extraction of image resources obtained from different imaging technologies through the segmentation of regions of interest from a breast section, enabling an improved automatic identification of the breast lesions, since the images obtained by different technologies—or the respective regions of interest—become correlated (step d) through the previous segmentation (step c).

Also, an object of the present invention is a computer system for the improved identification of breast lesions which is configured to implement the method of the present invention in any of the described embodiments of the method.

It is also an object of the present invention a composite system for the improved identification of breast lesions comprising the computational system of the present invention and at least two different imaging technology equipment, said equipment preferably being magnetic resonance imaging, ultrasound and/or mammography.

It is a further object of the present invention to provide a non-transient memory path comprising executable program instructions for carrying out the method of the present invention in any of the described embodiments of the method.

DETAILED DESCRIPTION OF THE INVENTION

Figure 1:
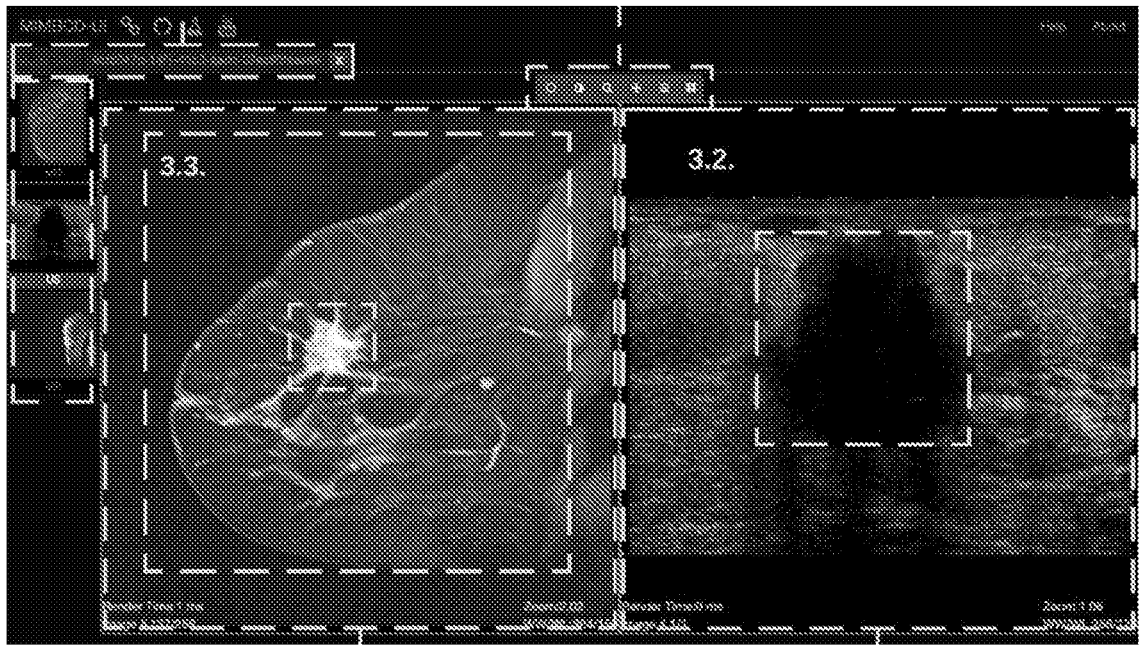
FIG. 1—two digital images of a breast section, obtained by magnetic resonance imaging (MRI) and ultrasound (US).
Figure 2:
FIG. 2—magnification of the digital ultrasound image in FIG. 1, with the superimposition of a geometric figure consisting of a polygon, a pentagon, and which provides support for segmentation.
Figure 2:
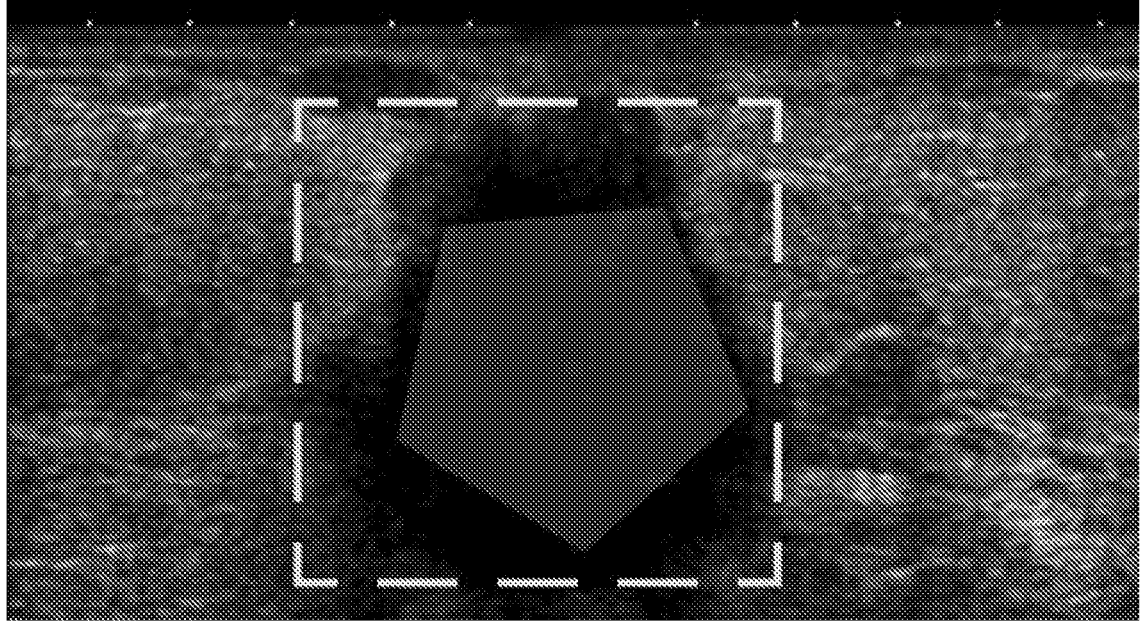

The general embodiments of the present invention are described in the Summary of the Invention. Such embodiments are detailed below, according to other advantageous and/or preferred embodiments of the present invention.

In a preferred mode of the method of the present invention, the clinical process of segmenting digital image regions of a breast section is performed using a geometric shape, the geometric shape preferably consisting of one or more polygons, eccentric sections, or combinations thereof.

In an inventive aspect of the present invention, the segmentation comprises determining at least one parameter of said sections, said parameter consisting of a volume shape, contour and/or contour point of each section.

In another inventive method aspect of the present invention, the segmenting of each section comprises determining one or more points associated with said section and, based on that determination, generating a contour and/or volume shape of the section.

In another inventive method aspect of the present invention, said correlation comprises the implementation of at least one Artificial Intelligence algorithm, Machine Learning and/or Deep Learning on said segmented sections.

Preferably, the segmentation process is performed based on at least one user interaction. Additionally, in a preferred embodiment, the user interaction is obtained from user definition of a shape volume, contour, interior point and/or contour point of each section. Additionally, in another preferred embodiment, by definition, user interaction is obtained from freehand region drawing and or at least a marking of a point in the image.

In another inventive method aspect of the present invention, said freehand definition is performed to annotate a section associated with a potential breast cancer lesion mass or dot denoted on the image, where the clinician is performing annotations of a potential microcalcification of a breast cancer lesion.

Preferably, imaging technologies comprise mammography, ultrasound and/or magnetic resonance imaging.

EMBODIMENTS

More specific embodiments of implementing the method and system of the present invention are described below.

The present invention operates with standard formats supported by medical images, including MG, US and MRI modalities.

These modalities are typically available—in the equipment that obtains them—in the standard format of Digital Image and Communication in Medicine (DICOM) and are supported in a single modality by the existing systems.

Furthermore, most systems are general-purpose and do not adapt to specific clinical domains (e.g., breast screening), not providing adequate support for different clinical workflows.

Using a tool that implements the method process and systems of the present invention, the clinical workflow includes and is enhanced by automated agents by integrating AI algorithms.

The present invention further includes a new framework for a standardized generation of an annotated medical image dataset of masses and calcifications relating to breast cancer lesions. This is represented as it can also function as a visualization of medical images used in a realistic clinical setting. Medical images and their annotations are presented in a multimodality strategy.

Additionally, the present invention may also include new annotation techniques for medical images: i) a freehand polygon tool for annotating the masses of breast cancer lesions; and ii) a dot marking on the image to denote the calcifications from breast cancer lesions.

With a dataset generated using this new methodology process, the clinical workflow integrates AI algorithms that compute the segmentation and classification of injuries by automatic agents, which also allows reducing healthcare costs and mitigating medical errors, while in the end the patient's healthcare will improve. The correlation resulting from the operation of an element as an AI allows for improved medical care, complementing specialized clinical knowledge to increase the performance and accuracy of diagnosis.

Figures 3, 4:
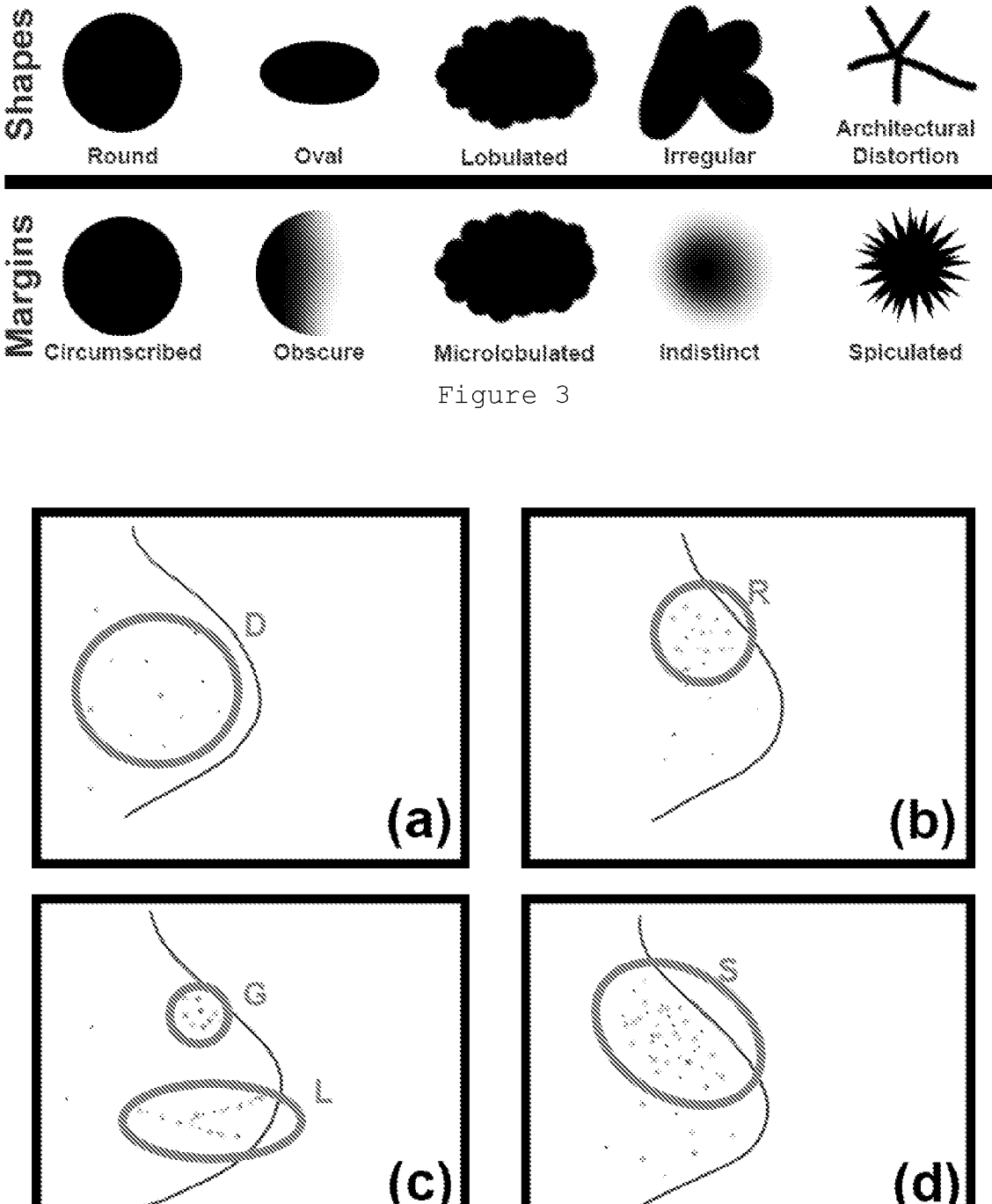
FIG. 3—representation of various polygons, eccentric sections and combinations of eccentric sections, as well as their designations, which are commonly identified and which provide support for segmentation.
FIG. 4—representation of different types of calcification identified in digital images of a breast section, in which the diffuse type a) presents randomly arranged calculi, the regional type b) presents calculi close to each other, typically forming a circle, the type of group c) has a small area, with few calculus, Linear type c) has inline calculus, and segment type d) is similar to regional, but with a more oval shape instead of circular.
Figure 5:
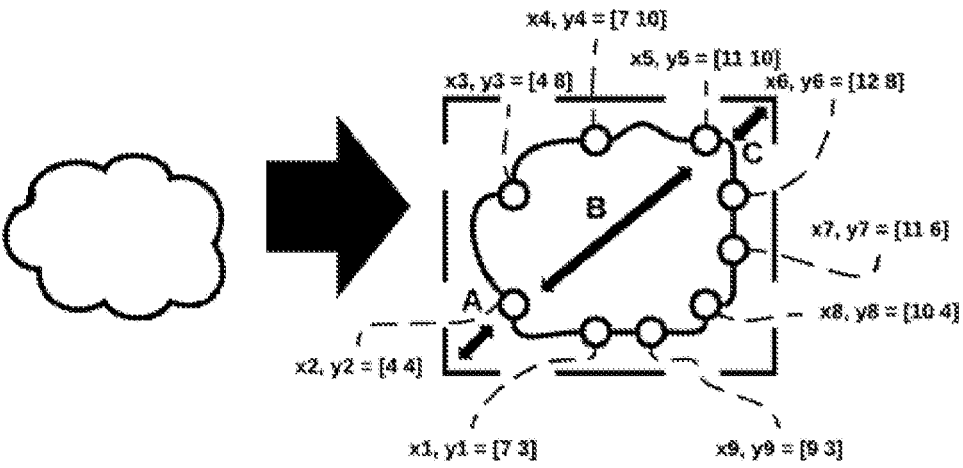
FIG. 5—representation of a lesion identified in a region of interest, in which the gray area is the lesion, which is parameterized through a shape volume (surrounding rectangle), contour (surrounding contour of the lesion) and/or point of contour of each section (several contour points). Contour points can be characterized using coordinates x, y, or, in the various examples of coordinate pairs, x1, y1; x2, y2; x3, y3; x4, y4; x5, y5; x6, y6; x7, y7; x8, y8; x9, y9. The diameter of the contour (A) and the distances from the contour to the vertices of the shape volume (B, C) can also be identified.

Annotations such as those depicted in FIG. 5 are particularly useful for extracting features such as contours, intersections, shapes (FIG. 3), and image patterns (FIG. 4). For a proper correlation/classification made by automatic agents, this can be used in the process of delimitation and segmentation of lesions.

Through the method of the present invention, a user can interact with a user interface by making annotations (FIG. 5), which can be connected (for example, using freehand for masses) or not (for example, using dot marking feature for calcifications) on the contours of the lesion.

Each mark/marker dot is referenced to a pair of coordinates x, y. The coordinates x, y define a position in the image.

Thus, it is possible to measure the ground-truth of the lesion, that is, the shape volume (FIG. 5), and provide this information to the algorithms that correlate this information. Furthermore, it allows for an autonomous classification of the margins and shapes of the masses (FIG. 3) and distribution patterns of calcifications (FIG. 4).

The present invention can be applied in i) Analysis of medical images; ii) computer-aided diagnosis (CADx); iii) breast cancer screening; or iv) AI-based medical imaging assistants.

In radiologic analysis, technologies are based on medical images, in which they identify anomalies and diseases more accurately than doctors. Such tools are made to satisfy the basic tumor metrics of small cancer. In addition, compatibility with common image analysis tools facilitates radiologist involvement in curating image data, including image annotation. Image annotation datasets support the development and evolution of AI applications for medical imaging.

CADx tools are used for diagnosing breast cancer, lung cancer, etc. A CADx identifies abnormal signs as soon as a human professional fails. These tools are designed to deliver accurate and powerful healthcare solutions designed by experts to optimize operational efficiency, clinician confidence and patient outcomes. With the present invention, it is possible to easily extend current capabilities to a CADx system.

In the field of breast cancer screening, a set of tools for estimating the severity of a breast cancer lesion is shown. These tools are intended to look for patterns about the disease before a person has symptoms, which the present invention promotes. With the present invention, the community will achieve this with a method that will promote the generation of a dataset with relevance in medical images.

In the field of clinicians based on AI medical imaging, medical applications are designed to optimize productivity and speed up the diagnostic task with a range of imaging tools for any type of study mode on a workstation. From these tools, the AI is able to interact seamlessly with users via text, streamline the necessary information at the relevant service points or provide clinical decision support with reading devices. The present invention enhances this functionality by offering, e.g., radiologists, a higher data relevance.

As will be apparent to one skilled in the art, the present invention should not be limited to the embodiments described herein, and several changes are possible that remain within the scope of the present invention.

Evidently, the preferred modes presented above are combinable, in the different possible ways, avoiding here the repetition of all these combinations.

Lisbon, Oct. 27, 2021.

The invention claimed is:

1. A computer implemented method for improved identification of breast lesions via multimodal imaging, the method comprising performing, by a computer system comprising a processor, a storage unit including recorded program instructions to implement the method, and means of visualization of medical images, the steps of:

a) obtaining by the processor a plurality of digital images of a breast section, at least two of these images being obtained by different imaging technologies, b) registering by the processor one or more regions of interest in the digital images of a breast section, to be identified, c) segmenting by the processor said regions of interest, thus obtaining segmented regions, and determining, by the processor, geometric shapes of each of the segmented regions, each of the geometric shapes consisting of one or more polygons, d) correlating by the processor the segmented regions of the various digital images obtained by at least two different imaging technologies based on the determined geometric shapes of each of the segmented regions and, e) based on said correlation, identifying by the processor one or more breast lesions by means of said geometric shapes, and presenting by the processor one of said geometric shapes in the segmented regions of at least one of said digital images obtained by at least two different imaging technologies, in the means of visualization of medical images.

2. The computer implemented method according to claim 1, characterized in that said correlation comprises implementing at least one artificial intelligence, machine learning and/or deep learning algorithm on said segmented sections.

3. The computer implemented method according to claim 1, characterized in that said segmentation is performed based on at least one interaction.

4. The computer implemented method according to claim 3, characterized in that said user interaction is obtained from the definition, by said user, of a shape volume, a contour, an interior point and/or contour point of each region.

5. The computer implemented method according to claim 4, characterized in that said definition by a user is obtained from the definition by a freehand drawing and/or at least a marking of a dot on the image.

6. The computer implemented method according to claim 5, characterized in that said freehand definition is performed to annotate a section associated with a potential breast cancer lesion mass and said marking of a dot on the image is performed to annotate a potential lesion calcification of breast cancer.

7. The computer implemented method according to claim 1, characterized in that said imaging technologies comprise imaging by mammography, ultrasound and/or magnetic resonance.

8. A computer system for the improved identification of breast lesions via multimodal imaging, characterized in that the computer system comprises a processor, a storage unit and means of visualization of medical images, the processor being is-configured and the storage unit including recorded program instructions for implementing a computational method for improved identification of breast lesions comprising the steps of:

a) obtaining by the processor a plurality of digital images of a breast section, at least two of these images being obtained by different imaging technologies, b) registering by the processor one or more regions of interest in the digital images of a breast section, to be identified, c) segmenting by the processor said regions of interest, thus obtaining segmented regions, and determining, by the processor, geometric shapes of each of the segmented regions, each of the geometric shapes consisting of one or more polygons, d) correlating by the processor the segmented regions of the various digital images obtained by at least two different imaging technologies based on the determined geometric shapes of each of the segmented regions and, e) based on said correlation, identifying by the processor one or more breast lesions by means of said geometric shapes, and presenting by the processor one of said geometric shapes in the segmented regions of at least one of said digital images obtained by at least two different imaging technologies, in the means of visualization of medical images.

9. A composite system for the improved identification of breast lesions via multimodal imaging characterized in that it comprises at least two different imaging technology equipment, said equipment preferably being of imaging by mammography, ultrasound and/or magnetic resonance and a computer system for the improved identification of breast lesions, wherein the computer system further comprises a processor, a storage unit and means of visualization of medical images, the processor being configured and the storage unit including recorded program instructions for implementing a computational method for improved identification of breast lesions comprising the steps of:

a) obtaining by the processor a plurality of digital images of a breast section, at least two of these images being obtained by different imaging technologies, b) registering by the processor one or more regions of interest in the digital images of a breast section, to be identified, c) segmenting by the processor said regions of interest, thus obtaining segmented regions, and determining, by the processor, geometric shapes of each of the segmented regions, each of the geometric shapes consisting of one or more polygons, d) correlating by the processor the segmented regions of the various digital images obtained by at least two different imaging technologies based on the determined geometric shapes of each of the segmented regions and, e) based on said correlation, identifying by the processor one or more breast lesions by means of said geometric shapes, and presenting by the processor one of said geometric shapes in the segmented regions of at least one of said digital images obtained by at least two different imaging technologies, in the means of visualization of medical images.

10. The computer implemented method according to claim 1, wherein the shape volume consists of a combination of said one or more polygons and one or more eccentric sections.

\* \* \* \* \*